United States Patent [19]

Jurisch

[11] 4,107,171

[45] Aug. 15, 1978

[54] ALKANOLAMINE DERIVATIVES

[75] Inventor: Louis A. Jurisch, Marengo, Ill.

[73] Assignee: IMC Chemical Group, Inc., Terre Haute, Ind.

[21] Appl. No.: 750,080

[22] Filed: Dec. 13, 1976

Related U.S. Application Data

[60] Continuation-in-part of Ser. No. 652,432, Jan. 26, 1976, abandoned, which is a division of Ser. No. 601,699, Aug. 4, 1975, Pat. No. 3,994,919.

[51] Int. Cl.$^2$ .................................. C07D 263/06
[52] U.S. Cl. .................. 260/307 FA; 106/186; 106/311; 260/18 N; 260/18 EP; 260/22 R; 260/23 XA; 260/405.5
[58] Field of Search ............... 260/307 FA, 405.5

[56] References Cited

U.S. PATENT DOCUMENTS 3,994,919  11/1976  Jurisch .................. 260/307 F

*Primary Examiner*—Raymond V. Rush
*Attorney, Agent, or Firm*—Robert H. Dewey; Howard E. Post

[57] ABSTRACT

A product obtained by reacting an alkanolamine represented by the formula

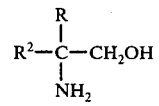

where R is methyl, ethyl or hydroxymethyl and $R^2$ is hydrogen, methyl or hydroxymethyl, with oiticica oil at ambient temperatures or above having utility as a dispersing agent in water-based paints.

7 Claims, No Drawings

ALKANOLAMINE DERIVATIVES

CROSS-REFERENCE TO RELATED APPLICATIONS

This application is a continuation-in-part of Ser. No. 652,432, filed Jan. 26, 1976 and now abandoned, which was a division of copending Ser. No. 601,699, now U.S. Pat. No. 3,994,919, filed Aug. 4, 1975.

BACKGROUND OF THE INVENTION

This invention relates to dispersing agents. In a particular aspect this invention relates to polymerizable alkanolamine derivatives having utility as dispersing agents.

Powder coatings were developed as an alternative to solvent based coatings as a means of eliminating the volatile solvents from the environment. The development has been described by Emory P. Miller and David D. Taft in "Fundamentals of Powder Coatings," published by the Society of Mechanical Engineers, 20501 Ford Road, Dearborn, Michigan, 1974. The coating is formulated as a dry powder consisting of one or more thermoplastic or thermosetting resin film-formers, or binders, and the pigments necessary to give the desired color. Sometimes a plasticizer for the film-former is included. These materials are finely comminuted and are applied to a metallic substrate by such methods as the fluidized bed process, electrostatic powder spraying, electrostatic fluidized bed and other electrostatic application methods.

Such coatings have been very successful but several problems have been encountered; also the equipment required to operate the various processes is very expensive. One of the most vexing problems is that of segregation of powders of different densities. It has been found that the ingredients must all have nearly equivalent densities to prevent segregation and subsequent non-homogeneous coating.

Another problem encountered is that of difficulty in controlling the film thickness. For example, when the powder is applied by electrostatic attraction, any inadequacies involved in applying the electrostatic charge will lead to uneven coating thickness. Also there is an inherently maximum film thickness which may prove inadequate for the anticipated use. Other problems involve those of occupational hygiene due to dust in air and the risk of explosion of the dusts. Accordingly an improved and a less expensive process is needed to utilize these coatings to the best advantage.

It is known from U.S. Pat. Nos. 3,737,401 and 3,787,230 to apply these powder coatings, not only in dry form but also wet with a liquid which is not a solvent for the particles. These patents are incorporated herein by reference thereto. According to these patents, the powders are slurried in the liquid without use of a suspending of dispersant agent. Such slurries have many disadvantages, such as lack of stability. On the other hand, the use of any of the common dispersing agents weakens the film and renders it water sensitive because the dispersing agent remains in the film after baking but does not of itself contribute to the strength, durability and water resistance possessed by the film-formers. Also some of these dispersants migrate to the surface, giving it a greasy feel, and they also attract dirt, thus marring the appearance.

E. P. Hoffman and R. P. Sikorski in the U.S. Pat. No. 3,787,230 proposed as a solution to these problems to form a slurry of the powder paint in water using a surfactant known as AEROSOL-T, a polypropylene base, non-water soluble powder. Although successful coatings are applied by this method, it suffers from the disadvantage that the slurries are not stable, i.e. the powder paint particles rapidly separate from the aqueous slurry, so best results are obtained only while continuously agitating the slurry during the coating process.

SUMMARY OF THE INVENTION

It is an object of this invention to provide novel dispersing agents.

It is another object of this invention to provide polymerizable dispersing agents.

It is still another object of this invention to provide stable water-dispersible coatings and thereby avoid expensive electrostatic application equipment.

It is still yet another object of this invention to provide water-dispersible coatings employing a dispersing agent wherein the dispersing agent is also a film-former.

Other objects of this invention will be apparent to those skilled in the art.

It is the discovery of the present invention to provide a compound obtained by reacting oiticica oil with an alkanolamine represented by the formula

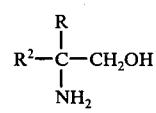

where R is methyl, ethyl or hydroxymethyl and $R^2$ is hydrogen, methyl or hydroxymethyl at ambient temperatures or above.

It is another embodiment of this invention to provide tris-oxazolidino derivatives of 4-keto-9,11,13-octadecatrienoic acid triglyceride. These compounds are excellent dispersing agents having particular utility in water-based coatings, especially coatings which are to be baked, e.g. water dispersions of powder coating. The dispersant of this invention is non-volatile and polymerizes during the baking step to form a component of the coating. The dispersant is non-migrating and does not come to the surface, as do other surfactants.

DETAILED DISCUSSION

It is the first embodiment of the present invention to provide dispersants and suspending agents for providing stable slurries of powder paints in water. Advantageously, these slurries may be prepared and stored for a considerable length of time with no significant separation of the powder paint.

The dispersants of the present invention are employed in an amount sufficient to provide the desired degree of stability of dispersion. Generally an amount of about 5–15%, preferably about 10% based on the weight of the powder paint, is sufficient. The amount of water employed is selected to provide the desired spraying characteristics. It is contemplated that suspensions of low water content will be prepared by the manufacturer and diluted by the user to fit his needs. Generally a suspension wherein the water content comprises 40–60% by weight has a suitable spraying viscosity.

The compounds of the present invention are of the class of compounds generally designated as oxazolidines. They can be readily prepared by the method of M. Senkus, J. Am. Chem. Soc. 67, 1515–1519 (1945), or William B. Johnston, U.S. Pat. No. 2,448,890, which are incorporated herein by reference thereto. Briefly, the compounds are prepared by reacting in a suitable solvent, e.g. an aromatic hydrocarbon such as benzene, toluene or xylene, an amino alcohol represented by the formula

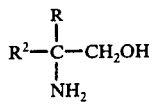

with oiticica oil. Thus the alkanolamines suitable for the practice of this invention include ethanolamine, 2-amino-1-propanol, 2-amino-2-methylpropanol, and 2-amino-1-butanol. These alkanolamines are known in the art and some are commercially available. The preferred compound is that prepared from 2-amino-2-methyl-1-propanol.

Oiticica oil is known in the art and is commercially available. It is obtained from the seeds of hicania rigida. It is composed principally of the triglyceride of licanic acid (4-keto-α-elaeostearic acid, or, more precisely, 4-keto-9,11,13-octadecatrienoic acid).

Accordingly it is an embodiment of this invention to provide the tris-oxazolidino derivatives of 4-keto-9,11,13-octadecatrienoic acid triglyceride by reacting the triglyceride with an alkanolamine represented by the above formula.

Oiticica oil also contains a lesser amount of the triglyceride of elaeostearic acid. Although the latter compound does not form an oxazolidine, it polymerizes during the baking step and forms an integral part of the coating. Oiticica oil is described by T. P. Hilditch and P. N. Williams in "The Chemical Constitution of Natural Fats," 4th Ed., John Wiley & Sons, Inc., New York, pp. 243–4, 253, 468–9 and 635.

The resins used in the practice of this invention are fusible thermosetting and thermoplastic resins. The resins used include but are not limited to polyvinyl chloride, ethylenevinyl chloride copolymers and vinyl acetate-chloride copolymers, including those modified by one or more additives, e.g. maleic anhydride; esters of cellulose such as cellulose acetate, cellulose acetate-butyrate, cellulose propionate, and cellulose butyrate; polypropylene; the polyamides such as nylon 6, nylon 11, and nylon 12; polyesters such as those obtained by esterifying mixtures of polybasic organic acids and polyols, especially the high molecular weight polyethylene terephthalates or isophthalates; the epoxy resins such as the diglycidyl ethers of bisphenol A, the novolac epoxy resins, or the cycloaliphatic epoxy resins formed by the reaction of cyclic olefins with peracetic acid, and curing agents therefore, such as aliphatic or aromatic amines, acid anhydrides and boron trifluoride; acrylics such as the lower aliphatic acrylic and methacrylic esters and amides.

Any of the powder coatings of the prior art can be used in the practice of this invention because they can be easily dispersed with the vinyl oxazolidines without regard to the resin involved. The coated substrate is then heated to a temperature sufficient to fuse the powdered coating, then cooled.

The invention will be better understood by reference to the following examples. It is understood, however, that the examples are intended only to illustrate the invention and are not intended to be limiting.

EXAMPLE 1

2-Amino-2-ethyl-1,3-propanediol (AEPD), 240 g (2 moles) was dissolved in 275 g of distilled water. Dibutyl hydrogen phosphate, 2 g, and triethyl phosphite, 0.2 g, were added and the solution was chilled in an ice bath. Acrolein, 110 g (1.97 moles) containing 0.1% hydroquinone as a polymerization inhibitor was added dropwise over a 30 min period with constant agitation. The agitation was continued for another 15 min at which time the reaction was adjudged to be complete. The solution contained 50±% water.

A commercial, clear powder, 19 g, intended for electrostatic spray (the powder used was an epoxy phenolic No. 464–84A marketed by Schenectady Chemicals, Inc., Schenectady, N.Y.) was mixed with 1 g of the vinyl oxazolidine solution obtained above and 10 g of distilled water were added. The mixture was stirred until the powder was completely wetted. The additional water was added to produce the desired viscosity; pumpable slurry was obtained with 8 g, a smooth latex with 12 g, and sprayable paint with 15 g of water.

The suspension was applied as a spray to a steel panel. The panel was baked for 15 min in a 400° F oven, then quenched by immersing in cool water.

The suspension provided a hard, smooth coating 1.2 ml thickness having a high gloss. It could withstand an impact of 160 in/lb, both direct and reverse.

EXAMPLE 2

The experiment of Example 1 was repeated in all essential details except that oiticica oil was substituted for acrolein on a ketone-equivalent basis and 2-amino-2-methyl-1-propanol (AMP) was substituted for AEPD. Also the step of chilling the acrolein was not carried out with oiticica oil.

Oiticica oil 1200 g was mixed with AMP 400 g equivalent to 267 g per mole of the alkanolamine in 50 g of benzene. The mixture was heated to 110° C in a reaction vessel equipped with a distillation column and a decantation take-off head. The water-benzene azeotrope was collected in the head and the benzene was returned to the reaction vessel. The temperature was slowly raised to 130° C while continuing to remove water. After water stopped coming off, all volatiles were stripped and nitrogen was sparged through the product to finish stripping the benzene.

The product was used as a dispersing agent for suspending a powder paint, commercially identified as Dri-Dex Gray, a product of Midland Dexter Corporation, in water in the following proportions:

| Dispersing agent | 2 parts |
|---|---|
| Powder paint | 18 |
| Water | 20 |

The resulting suspension was a loose, thixotropic gel which sprayed well onto a steel panel. The film after baking 2 min at 450° F was fully satisfactory.

EXAMPLE 3

The experiment of Example 2 is repeated in all essential details except that ethanolamine is substituted for AMP on an equi-molar basis. The product is used as a dispersing agent for suspending a commercially-available powder paint in water. The film after baking is fully satisfactory.

EXAMPLE 4

The experiment of Example 2 is repeated in all essential details except that 2-amino-1-propanol is substituted for AMP on an equi-molar basis. The product is used as a dispersing agent for suspending a commercially-available powder paint in water. The film after baking is fully satisfactory.

EXAMPLE 5

The experiment of Example 2 is repeated in all essential details except that 2-amino-1-butanol is substituted for AMP on an equi-molar basis. The product is used as a dispersing agent for suspending a commercially-available powder paint in water. The film after baking is fully satisfactory.

EXAMPLE 6

The experiment of Example 2 is repeated in all essential details except that 4-keto-9,11,13-octadecatrienoic acid triglyceride is substituted for oiticica oil on a ketone-equivalent basis. The product is used as a dispersing agent for suspending a commercially-available powder paint in water. The film baking is fully satisfactory.

EXAMPLE 7

The experiment of Example 6 is repeated in all essential details except that ethanolamine is substituted for 2-amino2-methylpropanol. The product is used as a dispersing agent for suspending a commercially-available powder paint in water. The film after baking is fully satisfactory.

EXAMPLE 8

The experiment of Example 6 is repeated in all essential details except that 2-amino-1-propanol is substituted for 2-amino-2-methylpropanol. The product is used as a dispersing agent for suspending a commercially-available powder paint in water. The film after baking is fully satisfactory.

EXAMPLE 9

The experiment of Example 6 is repeated in all essential details except that 2-amino-1-butanol is substituted for 2-amino-2-methylpropanol. The product is used as a dispersing agent for suspending a commercially-available powder paint in water. The film after baking is fully satisfactory.

I claim:

1. A product obtained by reacting an alkanolamine represented by the formula

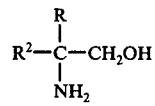

where R is methyl, ethyl or hydroxymethyl and $R^2$ is hydrogen, methyl or hydroxymethyl, with oiticica oil in a ratio of 267 g per mole of alkanolamine at temperatures of 110° to 130° C in the presence of benzene, toluene, or xylene solvent.

2. The product of claim 1 wherein R of said alkanolamine is methyl.

3. The product of claim 1 wherein R of said alkanolamine is ethyl.

4. The product of claim 1 wherein R of said alkanolamine is hydroxymethyl.

5. The product of claim 1 wherein $R^2$ is hydrogen.

6. The product of claim 1 wherein $R^2$ is methyl.

7. The product of claim 1 wherein $R^2$ is hydroxymethyl.

* * * * *

UNITED STATES PATENT AND TRADEMARK OFFICE
CERTIFICATE OF CORRECTION

PATENT NO. : 4,107,171
DATED : August 15, 1978
INVENTOR(S) : Louis A. Jurisch

It is certified that error appears in the above–identified patent and that said Letters Patent are hereby corrected as shown below:

Column 1, line 57, "of" should read -- or --

Column 5, line 26, following "film", insert -- after --

Column 5, line 31, "2-amino2" should read -- 2-amino-2- --

Signed and Sealed this

Twenty-fourth Day of April 1979

[SEAL]

Attest:

RUTH C. MASON
Attesting Officer

DONALD W. BANNER
Commissioner of Patents and Trademarks